(12) United States Patent
Göbel

(10) Patent No.: US 7,040,321 B2
(45) Date of Patent: May 9, 2006

(54) METHOD FOR CONTROLLING A VENTILATOR, AND SYSTEM THEREFOR

(75) Inventor: Fred Göbel, Weinheim (DE)

(73) Assignee: microcuff GmbH, Weinheim (DE)

( * ) Notice: Subject to any disclaimer, the term of this patent is extended or adjusted under 35 U.S.C. 154(b) by 94 days.

(21) Appl. No.: 10/109,554

(22) Filed: Mar. 28, 2002

(65) Prior Publication Data
US 2003/0000526 A1 Jan. 2, 2003

(30) Foreign Application Priority Data
Mar. 30, 2001 (DE) ................. 101 16 195

(51) Int. Cl.
*A61M 16/00* (2006.01)

(52) U.S. Cl. ............. 128/207.15; 128/204.18; 128/204.23; 128/207.14; 128/207.18

(58) Field of Classification Search .......... 604/96.01–103.14; 128/200.24, 203.12, 203.14, 128/203.24, 204.18–204.23, 204.29, 205.23, 128/207.14–207.18, 203.15, 203.21, 200.14, 128/202.15, 204.26, 205.11, 205.24; 606/191–200; 600/201, 204, 207

See application file for complete search history.

(56) References Cited

U.S. PATENT DOCUMENTS 5,487,383 A * 1/1996 Levinson ............... 128/207.15
5,752,921 A * 5/1998 Orr ........................... 600/533

FOREIGN PATENT DOCUMENTS

| DE | 32 04 110 | 8/1983 |
| DE | 197 24 096 | 12/1998 |
| DE | 198 45 415 | 9/1999 |
| EP | 022 144 | 1/1981 |
| EP | 459 284 | 12/1991 |
| WO | 94/22518 | 10/1994 |

* cited by examiner

Primary Examiner—Glenn K. Dawson
(74) Attorney, Agent, or Firm—Pauley Peterson & Erickson

(57) ABSTRACT

A method for controlling breathing gas flow of a ventilator for assisted or controlled ventilation of a patient as a function of a tracheobronchial airway pressure of the patient. A ventilator tube, such as a tracheal tube or tracheostomy tube, can be introduced into a trachea of the patient and subjected to the breathing gas, and has an inflatable cuff and at least one lumen that is continuous from a distal end of the tube to a proximal end of the tube. An apparatus detects an airway pressure, in which the tracheobronchial airway pressure is ascertained by continuous or intermittent detection and evaluation of an intra-cuff pressure prevailing in the cuff of the tube inserted into the trachea. The breathing gas flow of the ventilator is controlled as a function of the intra-cuff pressure detected.

20 Claims, 7 Drawing Sheets

METHOD FOR CONTROLLING A VENTILATOR, AND SYSTEM THEREFOR

BACKGROUND OF THE INVENTION

1. Field of the Invention

This invention relates to a method for controlling the breathing gas flow of a ventilator for assisted or controlled ventilation of a patient as a function of the tracheobronchial airway pressure of the patient, having a ventilator tube, such as a tracheal tube or tracheostomy tube, that can be introduced into the trachea or the patient and subjected to the breathing gas, that has an inflatable cuff and at least one lumen that is continuous from the distal end of the tube to the proximal end of the tube. This invention also relates to an apparatus for detecting the airway pressure, in which the tracheobronchial airway pressure is determined by continuous or intermittent detection and evaluation of the intra-cuff pressure prevailing in the cuff of the tube inserted into the trachea, and the breathing gas flow of the ventilator is controlled as a function of the intra-cuff pressure detected.

This invention also relates to a system for assisted or controlled ventilation of a patient, having a ventilator with a breathing gas source and a ventilator tube, which has an inflatable cuff with a supply line for compressed air, such as a tracheal tube or tracheostomy tube, which can be connected to the breathing gas source, an apparatus for detecting the airway pressure, and a control device which as a function of patient values, such as the airway pressure, controls the ventilator, or the supply quantity and composition of the breathing gas to the tube.

This invention also relates to the use of a ventilator tube, such as a tracheal tube or tracheostomy tube, or a gastric probe in a system for assisted or controlled ventilation of a patient with a ventilator.

2. Description of Related Art

A ventilator for assisted or controlled ventilation, with a ventilator tube and a breathing gas source that can be made to communicate with the ventilator tube and is controllable with patient values, is known from European Patent Disclosure EP 0 022 144 A1. With the aid of the control device of the ventilator, respiratory parameters such as tidal volume, respiratory rate, respiratory minute volume, flow pattern over time, end-inspiratory pause, amplitude of the breathing gas flow, pressure at the end of inspiration, peak pressure, PEEP pressure, idle volume in the ventilator, and ventilator compliance, can be adjusted.

In all the known ventilators and ventilation methods known, the so-called ventilation pressure, that is, the airway pressure (Presp) prevailing in the airways, is output as a parameter or is used as a parameter in the control algorithms of the ventilator. In clinical practice, Presp is typically ascertained inside the ventilator, or in the tubing leading to the patient. The airway pressure measured in the ventilator, because of the flow-dependent flow resistance inside the equipment, vent hoses, and ventilator tube, however, often differs considerably from the so-called central or tracheobronchial airway pressure (Ptrach) prevailing in the trachea of the patient. It is therefore difficult to draw a conclusion about the central airway pressure actually achieved in the trachea from the ventilation pressure measured inside the ventilator.

European Patent Disclosure EP 0 459 284 B1 teaches measuring the central airway pressure via a pressure measuring hose additionally placed in the trachea or in the tracheal tube, or via a fluid-filled pressure measuring conduit machined into the wall of the tracheal tube. The tracheobronchial airway pressure thus is intended to provide improved control of ventilators with supporting spontaneous breathing modes. A disadvantage in this measuring method for detecting the tracheobronchial airway pressure using pressure hoses in accordance with European Patent Disclosure EP 0 459 284 B1 is that the thin pressure measuring hoses, placed in the trachea in the tracheal tube, rapidly plug up with secretions on their end oriented toward the bronchial tube, and thus the central airway pressure can no longer be measured reliably. The pressure measuring hoses must be rinsed out from time to time. An apparatus according to European Patent Disclosure EP 0 459 284 B1 for measuring the tracheobronchial airway pressure using pressure measuring hoses or pressure measuring conduits that are filled with fluid has not yet gained acceptance, mainly because of the high cost of equipment and the expected vulnerability to malfunction, or the resultant measurement imprecision.

German Patent Disclosure DE-A 32 04 110 discloses a tracheal tube that includes a ventilation hose and a pressure measuring cannula for measuring the airway pressure. The pressure measuring hose ends inside the ventilator tube, at a distance from the distal end of the ventilator tube. This apparatus is again used to detect the airway pressure for regulating ventilation control with a ventilator. This apparatus for detecting the central airway pressure again has the disadvantage that the pressure measuring cannula, which is open on its end toward the bronchial tube, easily becomes plugged with secretions, making reliable, artifact-free measurement and regulation of the ventilator impossible.

PCT International Application WO 94/22518 teaches a ventilator tube which is used to control a ventilator. For continuous measurement of the central tracheobronchial airway pressure in assisted or controlled ventilation, the ventilator tube has a pressure sensor, located near the distal end of the ventilator tube. The pressure sensor is connected to an electronic signal processor, and the signal obtained is used to control various functions in the ventilator. Such a method is technologically complex and once again, because of deposits of secretion on the sensor, is adequately invulnerable to malfunction.

SUMMARY OF THE INVENTION

One object of this invention is to provide a method and a system with which the tracheobronchial airway pressure prevailing in the trachea of a patient to be ventilated can be determined and used to control the breathing gas supply to a ventilator, continuously and largely free of artifacts, without hindrance from secretions or transitory kinking of pressure measuring cannulas that are, for example integrated into the tube shaft. Based on known methods for controlling the breathing gas flow in a ventilator, this object is achieved according to this invention by determining the tracheobronchial airway pressure by continuous or intermittent detection and analysis of the intra-cuff pressure prevailing in the cuff of the tube inserted into the trachea. The flow of breathing gas in the ventilator is controlled as a function of the detected intra-cuff pressure.

Advantageous embodiments of the method of this invention are discussed in this specification and in the claims. A system for assisted or controlled ventilation of a patient with a ventilator having a breathing gas source and a ventilator tube according to this invention has a tube that can be introduced into the trachea and has a cuff of a microthin-walled elastic plastic film with a wall thickness of $\leq 0.02$ mm and can be subjected to a fill pressure $\leq 25$ mbar. There is a measuring instrument (electronic pressure transducer)

for detecting the intra-cuff pressure prevailing in the cuff of the tube, and the values for the intra-cuff pressure, ascertained continuously or intermittently by the pressure transducer unit, can be delivered to the control algorithms of the ventilator via a measuring line.

Also according to this invention, the use of a tracheal tube or tracheostomy tube with an inflatable cuff of a microthin-walled elastic plastic film with a wall thickness ≦0.02 mm, which cuff has a supply line for compressed air for setting a fill pressure of a maximum of 25 mbar and has a measuring instrument for continuous or intermittent detection of the intra-cuff pressure prevailing in the cuff, for controlling the breathing gas flow of a ventilator using the detected intra-cuff pressure in the tube introduced into the trachea of a patient.

The use according to this invention of a gastric probe, having an esophageally placed balloon of a microthin-walled elastic plastic film with a wall thickness of ≦0.02 mm is achieved. The gastric probe has a supply line for compressed air for setting a fill pressure in the balloon of approximately 25 mbar and a measuring instrument (electronic pressure transducer) for the continuous or intermittent detection of the esophageal pressure prevailing in the balloon, in order to control the breathing gas flow of a ventilator on the basis of the detected esophageal pressure of the balloon.

According to this invention, there is a method and a system for assisted or controlled ventilation by a ventilator and its control using tracheal tubes and tracheostomy tubes, which have microthin-walled cuffs or gastric probes that are equipped with a microthin-walled balloon. With the microthin-walled cuff or the esophageal balloon, the tracheobronchial airway pressure fluctuations, or the fluctuations in the intrathoracic pressure are detected and used to improve the interaction of the patient and the ventilator (respirator).

Tracheal tubes with a microthin-walled cuff are known from German Patent Disclosure DE 198 45 415 A1, and gastric probes that have an esophageal balloon are known from German Patent Disclosure DE 197 24 096 A1.

According to this invention, the tubes and gastric probes are used to detect the tracheobronchial airway pressure or thoracic pressure and have a measuring instrument for detecting the intra-cuff pressure prevailing in the cuff, or the esophageal pressure prevailing in the esophageal balloon, respectively.

The cuff or balloon for the tracheal tube/tracheostomy cannula, or the balloon for the gastric probe, is preferably made from a stretchable thin plastic film with a wall thickness of less than 0.02 mm, and in particular a wall thickness in the range from 0.01 to 0.005 mm. The cuff or balloon can be subjected, according to this invention, with a fill pressure of ≦25 mbar, and preferably to a fill pressure in the range between 10 and 20 mbar. The plastic film may comprise a thermoplastic polyurethane elastomer, and it should have a tension modulus of at least 10 MPa at 300% expansion in accordance with ASTM D 412.

According to this invention, particular mechanical properties of such microthin balloon films define one important field of use for controlling ventilators. The microthin-walled cuff or balloon of a ventilator tube or gastric probe makes it possible to detect pressure fluctuations inside the tracheobronchial airway, or inside the chest (intrathoracic pressure) with high measurement precision and over a wide amplitude range, largely without latency. The measurement option of such extremely thin-walled balloon films is possible due to their low operating pressures (fill pressures). Even at fill pressure values of 10 mbar, highly efficient sealing off from secretions, for example, or from the respiration pressure exerted on the balloon can be achieved with such balloons, even if the exerted pressure briefly exceeds the fill pressure of the balloon. Also, the membrane-like nature of such films makes it possible to detect even the tiniest pressure fluctuations inside the balloon, or structures communicating transmurally with the balloon, and submit them to a measurement.

The tracheobronchial or intrathoracic pressure is thus detectable continuously, in the form of a multiply usable parameter, for controlling the respiration of a ventilator or for monitoring the respiratory mechanics of a patient by detecting the intra-cuff pressure that prevails inside the cuff of the tube located in the trachea, or detecting the balloon pressure prevailing in a balloon placed inside the esophagus of the patient.

The detection according to this invention of the tracheobronchial pressure via the intra-cuff pressure or intrathoracic pressure via the esophageal balloon pressure opens up new options for a ventilator and for controlling the breathing gas flow.

According to this invention, by detecting the actually prevailing airway pressure in the tracheobronchial region, it is possible to control the ventilator-controlled ventilation gas flow to avoid overpressure situations inside the deep airways.

BRIEF DESCRIPTION OF THE DRAWINGS

This invention is described below along with further features, and including the details shown in the drawings, wherein.

DESCRIPTION OF PREFERRED EMBODIMENTS

Figure 5:
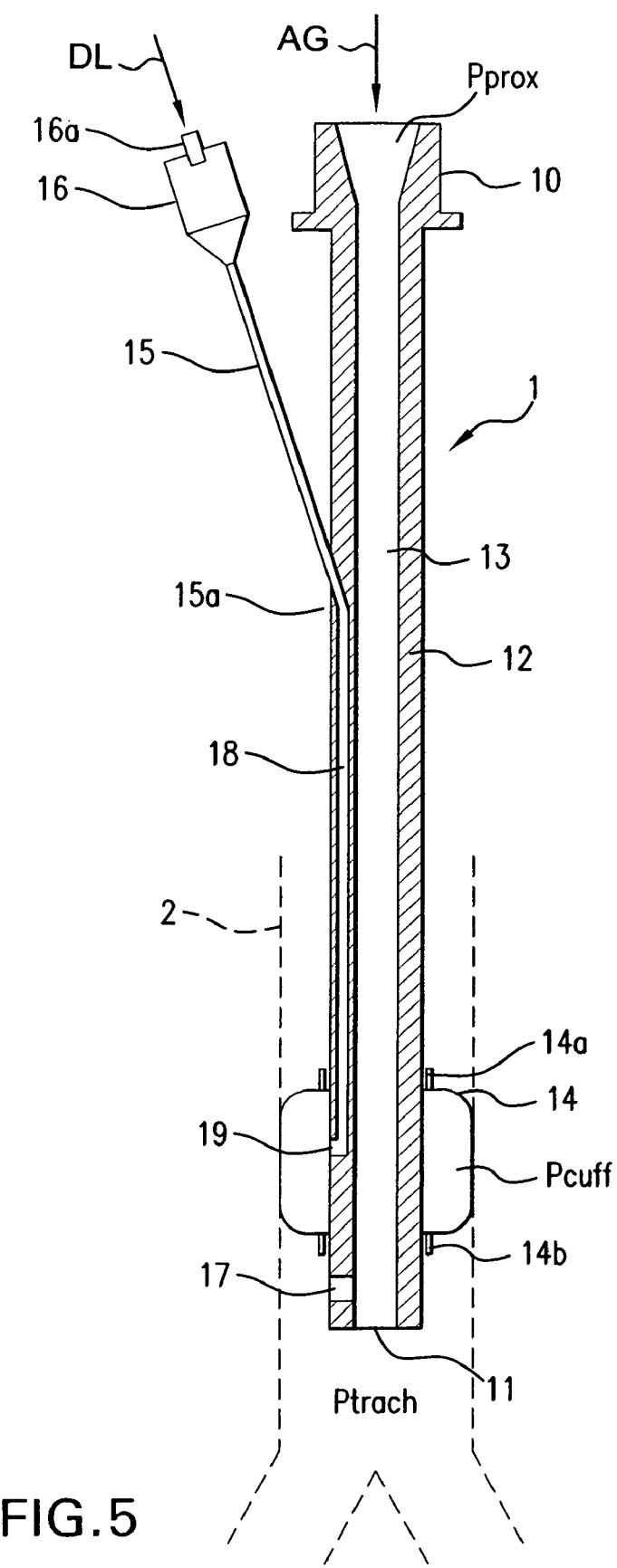
FIG. 5 schematically shows a tracheal tube with a cuff in longitudinal section.
Figure 6:
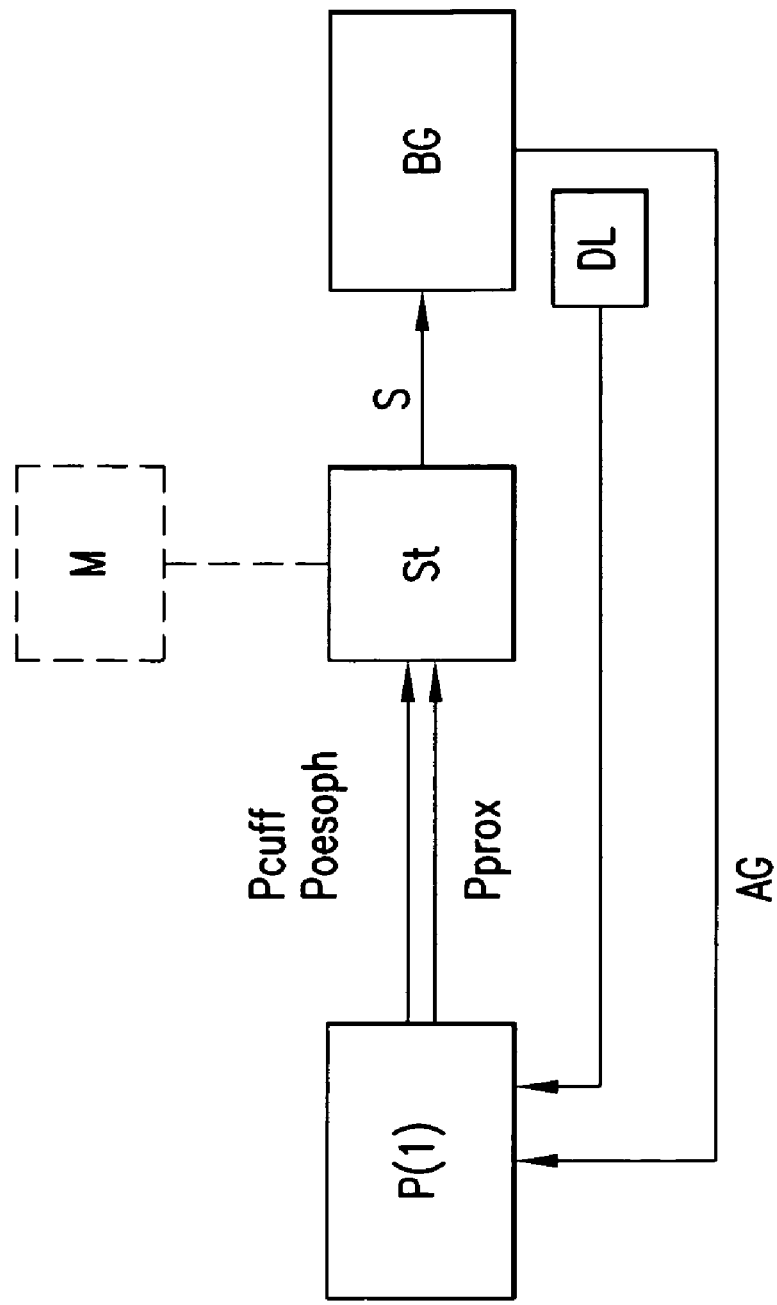
FIG. 6 is a block diagram showing assisted and controlled ventilation by a ventilator.
Figure 7:
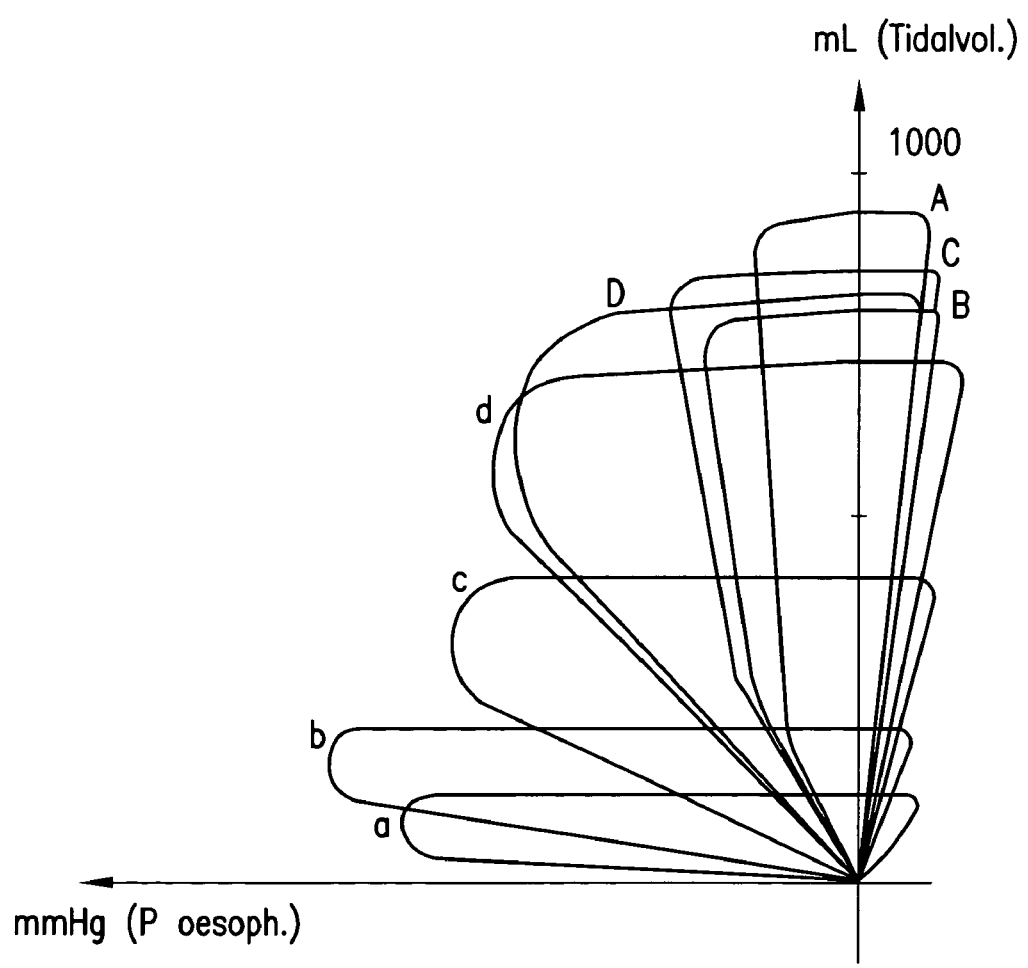
FIGS. 7 and 8 are work graphs illustrating various ventilation situations.
Figure 8:
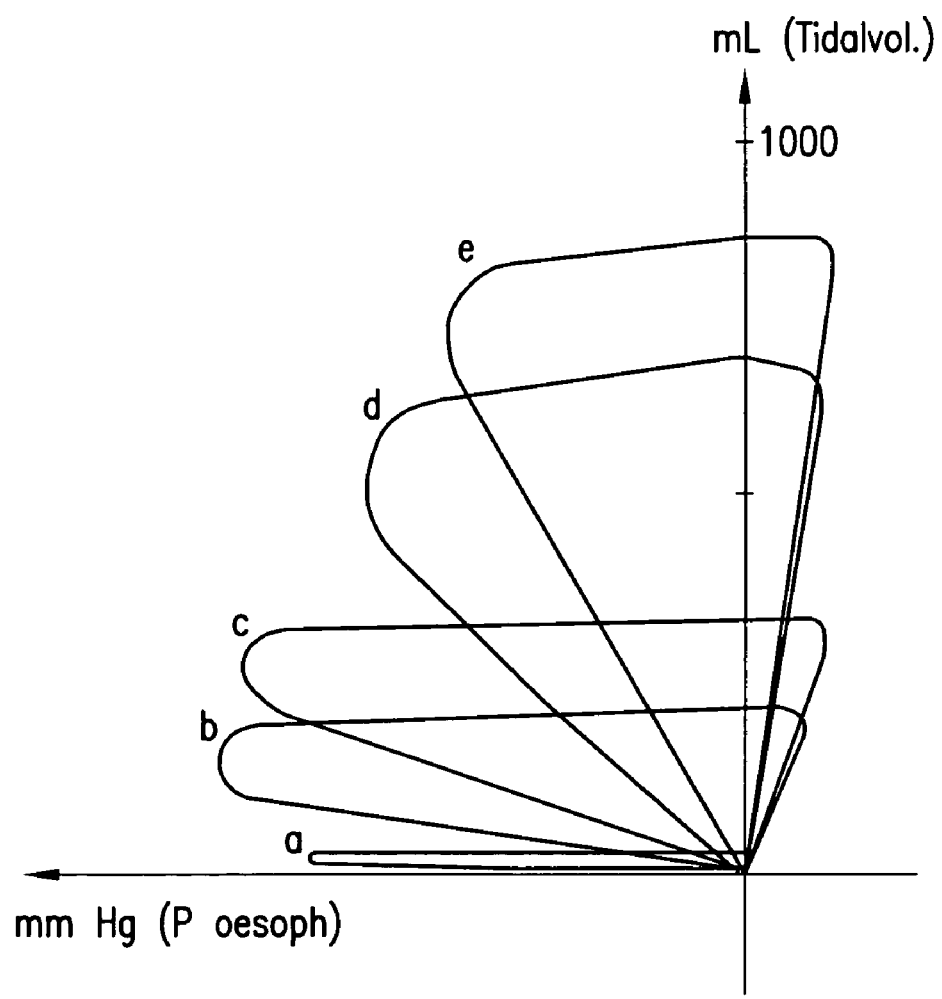

FIG. 6 shows a function diagram for assisted or controlled ventilation of a patient P, into whose trachea a tracheal tube 1, shown in FIG. 5, is introduced, in order to introduce the breathing gas AG and detect the airway pressure by suitable measuring instruments. On the one hand, the intra-cuff pressure Pcuff is detected continuously and delivered to a control device ST for the ventilator BG. The control device includes a measured value and signal processor with an evaluation unit, and in accordance with the detected intra-cuff pressure Pcuff, it furnishes a signal S for controlling the ventilator. This signal is used, for example to control either the trigger (tripping a ventilation stroke) in assisted ventilation, or the pressure limiting function (maximal or "upper ventilation pressure"), for example, which is included in all modes of ventilation. Accordingly, with this signal S, the supply of breathing gas AG from the ventilator BG to the patient P is controlled. It is also possible to equip the ventilator with a pressure regulator DR for the fill pressure FD of the cuff of the tracheal tube 1 as well, with which regulator the supply of compressed air DL for filling the cuff in accordance with the desired cuff pressure, such as 15 mbar in the neutral state (end of the exhalation phase of the patient), can be regulated. The pressure regulator can also be designed for periodic or intervallic readjustment of the desired cuff pressure, for instance at intervals of 60 seconds. A measuring instrument for detecting the ventilation pressure Pprox at the proximal end of the tube 1 is also provided, which furnishes a measured value to the control device ST. Furthermore, the control device can have a monitor M, on which work graphs are shown to illustrate the various ventilation situations, such as shown in FIGS. 7 and 8.

The measurement of the tracheobronchial airway pressure, which prevails at the distal end of the tube introduced into the trachea of a patient, is possible by using a tracheal tube 1, shown as an example in FIG. 5, with a microthin-walled cuff 14; the cuff fill pressure FD can be reduced to the very low range, from 10 to 25 mbar.

Figure 1:
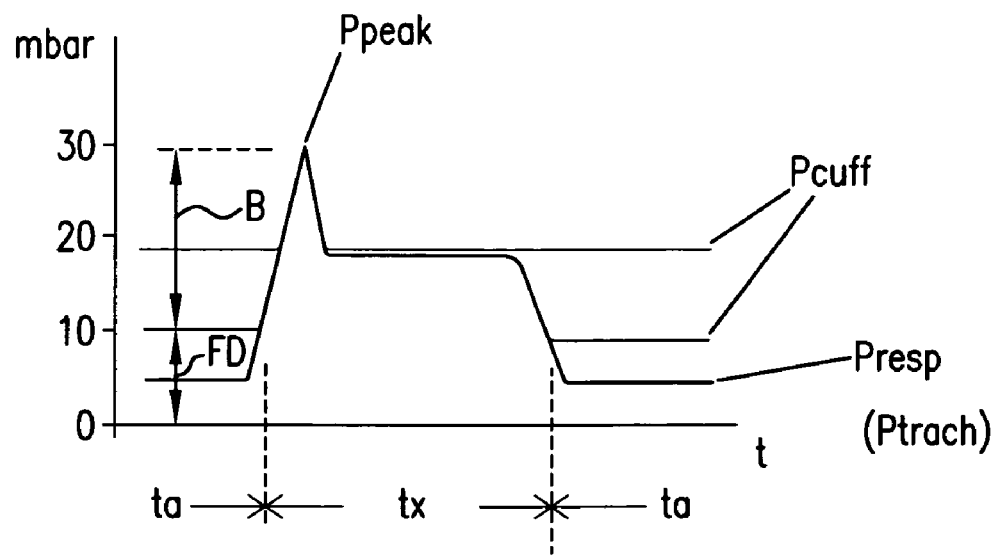
FIG. 1 is a graphical representation showing the course of the tracheobronchial airway pressure during a breathing stroke.

FIG. 5 shows the tracheal tube 1, with a lumen 13 that is continuous from the proximal end 10 to the distal end 11. A standardized tube connector 10, for instance for a Y-piece of the ventilation tubing, is provided on the proximal end. On this end, the ventilation pressure Pprox is detected by a measuring instrument, not shown, used to ascertain the flow resistance of the tube 1. Near the distal end 11, a through hole 17 is embodied in the wall 12 of the tube 1. On the outside near the distal end 11 of the tube 1, but before the through hole 17, the inflatable cuff 14, of a microthin plastic film comprising a thermoplastic elastomer, with a wall thickness of 0.005 mm, for example, is secured tightly to the tracheal tube 1 in the region 14a, 14b. A supply line for compressed air DL, with the aid of which the cuff 14 is inflated at a fill pressure FD, leads into the interior of the cuff. For supplying the compressed air to the cuff, a conduit 18 is, for example, machined into the wall of the tube 1 and emerges from the wall 12 of the tube 1 in the region of the cuff 14, through the opening 19. The conduit 18 leads in the direction of the proximal end 10 of the tube 1, and a supply line 15 for the compressed air is introduced into the conduit 18 at the point 15a. The proximal end of the supply line 15 has a monitoring balloon 16 and a connection 16a, through which the compressed air DL for inflating the cuff 14 is supplied when the desired fill pressure FD, such as 10 mbar, is reached. At the distal end of the tube 1, the tracheobronchial airway pressure Ptrach prevails. In the cuff 14, the intra-cuff pressure (Pcuff) prevails, which in the neutral state is equivalent to the fill pressure. If the tracheobronchial airway pressure Ptrach is higher than the intra-cuff pressure Pcuff of the cuff 14, which is equivalent to the fill pressure, then the higher tracheobronchial pressure Ptrach is transmitted to the cuff and raises the intra-cuff pressure until there is a pressure equilibrium, or in other words Pcuff is equal to Ptrach. This process that plays out during the ventilation is shown in FIG. 1. In FIG. 1, the tracheobronchial airway pressure and the intra-cuff pressure are plotted in mbar over one breathing stroke; the course over time t is plotted on the horizontal axis. The cuff fill pressure FD is 10 mbar, for example. During the neutral phase, without the delivery of breathing gas (end-expiratory phase), in the time periods ta, the intra-cuff pressure Pcuff equals the fill pressure of 10 mbar. During the breathing stroke, identified by the increase in the tracheobronchial airway pressure Presp up to the maximum airway pressure Ppeak, the intra-cuff pressure Pcuff increases analogously, practically without delay, because the tracheobronchial airway pressure is transmitted to the cuff without latency. During the period tx, the intra-cuff pressure Pcuff accordingly corresponds to the prevailing tracheobronchial airway pressure Presp (Ptrach).

The intra-cuff pressure (Pcuff) passively follows the airway pressure Presp. Because the tracheobronchial airway pressure Presp is transmitted in the region of the distal end of the tube introduced into the trachea to the cuff, or the intra-cuff pressure prevailing inside the cuff, without delay, the tracheobronchial airway pressure can be measured continuously in the range B in which Presp is greater than Pcuff, by detecting Pcuff. If the tracheobronchial airway pressure Presp exceeds the fill pressure FD in the cuff, then the intra-cuff pressure Pcuff follows the airway pressure exerted tracheobronchially on the cuff and presses the cuff with its microthin envelope against the tracheal wall with minimum delay. Because of the immediate, inertia-free deformation of the microthin-walled cuff, self-sealing is assured, which seals off from the exerted gas pressure reliably even in ventilation at a ventilation pressure that markedly exceeds the fill pressure of the cuff.

For recording the intra-cuff pressure, the ventilator can be expanded with a module with a pressure regulator which is integrated with the control device and sets the desired pressure in the cuff, automatically readjusts it, and continuously makes the intra-cuff pressure available, for instance in the form of a digitized signal, for controlling the ventilator.

On the basis of the continuous or intermittent measurement of the intra-cuff pressure with tracheal tube/tracheostomy cannulas with a microthin-walled cuff, the following functions can be performed for patients ventilated by machine: the tracheobronchial airway pressure Ptrach can be measured or calculated at the distal end of the tracheal tube; the upper ventilation pressure limit (Pmax) of the ventilator can be oriented to the measured intra-cuff pressure Pcuff, and thus to the tracheobronchial airway pressure Ptrach at the distal end of the tracheal tube; the ventilation, in pressure-supported or pressure-controlled ventilation methods, can be oriented to the measured intra-cuff pressure Pcuff and thus to the tracheobronchial airway pressure Ptrach at the distal end of the tracheal tube, as a target ventilation pressure to be reached; the pressure difference $\Delta P$ to be generated by the ventilator in order to overcome the flow resistance of the tracheal tube can be ascertained simply, by measuring the intra-cuff pressure Pcuff in accordance with the tracheobronchial airway pressure Ptrach, by subtracting it from the proximal airway pressure, and from one breathing stroke to another can thus be adapted to the particular current flow resistance of the tracheal tube; and on the basis of intrathoracic fluctuations caused by the mechanics of breathing, in the intra-cuff pressure Pcuff, the triggering of the ventilator can be accomplished synchronously with the instant of onset of the thoracic respiratory motion of the patient.

Figure 9:
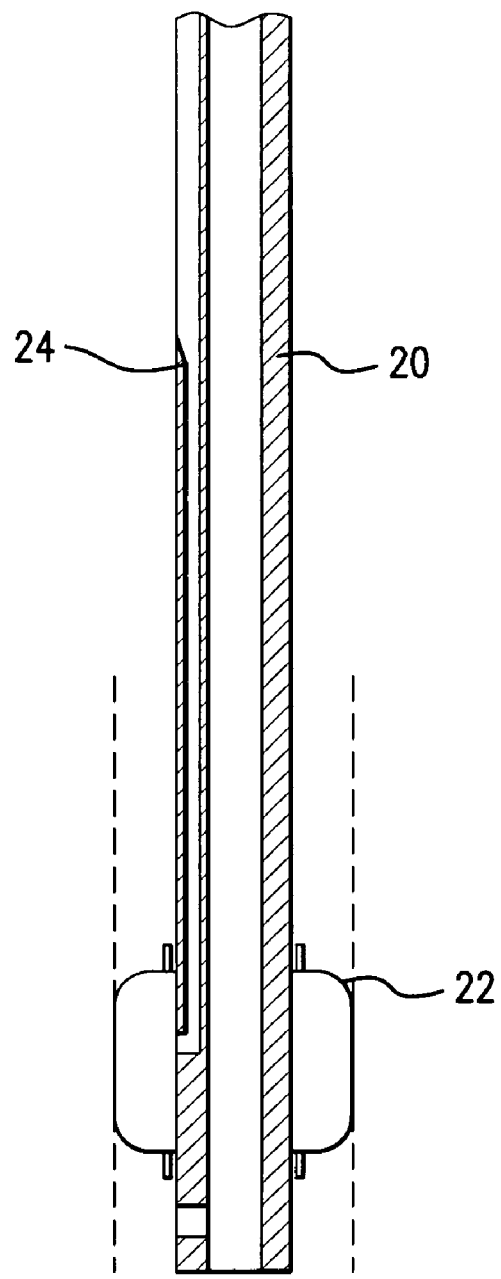
FIG. 9 shows a gastric probe with a balloon according to one embodiment of this invention.

In a further embodiment of this invention, for optimizing the control of the ventilator, a gastric probe, such as the gastric probe 20 shown in FIG. 9, for introduction into the esophagus of the patient can be provided, equipped with an inflatable balloon 22 that can be subjected to a fill pressure $\leq 25$ mbar through a fill lumen 24, and the esophageal balloon pressure prevailing in the balloon of the gastric probe can be ascertained continuously or intermittently. The gastric probe 20 can desirably be used in combination with any tube, such as described above, for insertion into a patient's trachea and having an inflatable cuff. The fluctuations in the intrathoracic pressure that are transmitted to the balloon of the gastric probe are detected and evaluated and supplied to the ventilator for controlling the breathing gas flow. By inflation of its esophageal balloon, the gastric probe that can be introduced into the esophagus is placed against the wall of the esophagus, which in its middle third and lower third transmits the pressure course inside the thorax through the wall of the esophagus (transmurally) to the esophageally placed balloon of the gastric probe. The transmurally transmitted pressure is picked up by this balloon and made usable as a measured value and control signal.

Because of the continuous characterization of the intraesophageal (intrathoracic) pressure course by the balloon of a gastric probe, which can also be a nutrition probe, with an esophageally placed balloon filled with a low pressure, it is possible: to optimize the synchronization of the ventilator and the patient, and for example to achieve latency-free triggering of the ventilator and the best possible calibration over time of the ventilation cycles or respiratory cycles of the ventilator and the patient, respectively; and to characterize the independent respiratory performance of the patient continuously over time and to gain parameters in the form of feedback for the therapist.

The ventilation planning ventilation should be oriented as closely as possible to the current respiratory capacity of the patient.

The proportion of the patient's independent respiratory performance that is not machine-supported should be neutralized, or reduced to the greatest possible minimum, by machine compensation, oriented to the course of the esophageal balloon pressure, of breathing strokes that are volumetrically ineffective or only minimally volumetrically effective, by supportive but volumetrically ineffective breathing strokes.

By the combined use, according to this invention, of such control of the course of ventilation, oriented to the intraesophageal balloon pressure, with monitoring of the respiratory work performed by the patient during ventilation, which according to this invention is particularly easy for the therapist and is intuitively accessible, one goal is to enable the earliest possible weaning of ventilated patients from the ventilator in a way that is oriented strictly to the success of ventilation, and particularly an increase in the patient's respiratory work.

In the method of this invention, the esophageal balloon pressure in the balloon of the gastric probe introduced into the esophagus is measured by a measuring instrument, and the measured values are transmitted by a measuring line that extends from the balloon to the ventilator or to a control device for the ventilator. The values obtained by measuring the esophageal balloon pressure are used to characterize the respiratory work done by the patient, and from pressure-supported respiratory cycles of fixed duration, cyclical respiratory work graphs are ascertained and displayed on a monitor in the form of pressure-volume loops.

The intra-cuff pressure of the tube is also measured by a measuring instrument, and the measured values are transmitted by a measuring line extending from the cuff of the tube to the ventilator, or to a control device for the ventilator. In order to detect the esophageal pressure, equivalent to an intrathoracic pressure, the system for assisted or controlled ventilation of a patient using a ventilator with an air source has a gastric probe with an inflatable balloon of a microthin-walled elastic plastic film with a wall thickness of $\leq 0.02$ mm, and the gastric probe balloon is subjected to a fill pressure of $\leq 25$ mbar. A measuring instrument for detecting the esophageal balloon pressure prevailing in the gastric probe balloon is also provided, and the values for the esophageal balloon pressure, detected continuously or intermittently by the measuring instrument, can be delivered to the control device of the ventilator via a measuring line. To set a desired fill pressure in the gastric probe balloon, a measuring and regulating device is provided, which is integrated with the control device of the ventilator. For setting a desired fill pressure in the cuff of the tube introduced into the trachea of a patient, it is also possible to provide a measuring and regulating device for the fill pressure, which is integrated with the control device of the ventilator.

By measuring the tracheobronchial airway pressure via the intra-cuff pressure in the cuff of the tube introduced into the trachea, it is possible according to this invention, for the pressure difference $\Delta P$ to be generated by the ventilator in order to overcome the flow-dependent flow resistance of the tube, to be ascertained in accordance with the pressure difference between pressure Pprox at the proximal end of the tube and the tracheobronchial airway pressure Ptrach at the distal end of the tube, by measuring the pressure at the proximal end of the tube and by measuring the intra-cuff pressure, and to be adapted to the applicable flow resistance of the tube from one breathing stroke to another during the ventilation with the ventilator.

It is also proposed that a certain differential value of the intra-cuff pressure be predetermined as a trigger threshold for the ventilator, and that it trip the supporting machine ventilation stroke if the intra-cuff pressure drops at the onset of inspiration, which is synchronous with the intrathoracic pressure drop. The values, obtained by measuring the intra-cuff pressure, can be used to control the "upper pressure limitation" (Pmax) function of the ventilator, so that on reaching a predetermined allowable upper airway pressure in the trachea that must not be exceeded, the ventilator either switches off the supply of breathing gas or switches over to exhalation.

The individual method steps and equipment options according to this invention are further explained below.

Orientation of the ventilator with respect to the pressure limitation of the upper ventilation pressure Pmax to the intra-cuff pressure Pcuff can be considered.

If the tracheobronchial airway pressure (Ptrach) exceeds an upper ventilation pressure value Pmax that is to be input at the ventilator, then the machine ventilation stroke ceases, or the valves of the ventilator switch to expiration for immediate relief. Conventional ventilators measure the airway pressure Presp at the proximal or outer end of the tracheal tube, or in the tubing of the ventilator. The airway pressure Ptrach that actually prevails in the lungs can not be ascertained directly by conventional equipment technology at the distal end of the tracheal tube. Known ventilators are thus equipped with an option for compensating for the flow-dependent tube resistance (automatic tube compensation), in the form of a computerized approximation of the airway pressure (Ptrach), prevailing at the distal end of the tube, by a compensating algorithm, which is oriented to the size of the tracheal tube used (inside diameter), which must be input manually in the ventilator when ventilation begins, and as a consequence is only oriented to the flows measured in the equipment.

The option of actually measuring the tracheobronchial airway pressure at the distal end of the tube by means of the tube cuff, in its function as a sensor element, offers the intra-cuff pressure as a reliable measurement variable for the function of an upper ventilation pressure limit (Pmax), or for the discontinuance of the machine breathing stroke, at critically high pressures.

Above all in ventilation using pediatric tubes with a very small inside diameter, in conventional ventilation partial shifting of the tube can easily occur, for example from secretions or kinking of the tube. The tracheobronchial airway pressure in conventional ventilation can thus deviate considerably from the proximal airway pressure measured before the tube. According to this invention, the tracheobronchial airway pressure, ascertained at the distal end of the tube via the intra-cuff pressure, and the measured proximal airway pressure of the tube are ascertained and compared by the control device of the ventilator. If a no longer plausible difference is exceeded, for instance if the pressure measured proximally before the tube is considerably higher than the airway pressure (intra-cuff pressure) or Ptrach measured at the distal end is implausibly higher than the pressure measured before the tube, then an alarm can be tripped.

A further option for the ventilator is to orient the desired ventilation pressure, in pressure-controlled or pressure-supported respiration, to the intra-cuff pressure. Ideally, the ventilation pressure to which the breathing gas supply to the patient is subjected should be oriented to the tracheobronchial airway pressure, not to a ventilation pressure (which as a rule deviates from it) of the kind that prevails for instance at the proximal end of the tube and is typically measured there. Particularly for ventilating children, this is decisive, because in children the airway pressure established tracheobronchially must not become overly high. Because tracheal tubes for children have a very small inside diameter, a backup pressure can easily build up between the distal end of the tube and the associated ventilation tracts, because of the high flow resistance of small tubes, a greater volume can enter the lungs upon active machine ventilation (inhalation) than can escape from the lungs upon the passive exhalation.

Orientation of the ventilator with respect to pressure support or pressure-controlled ventilation to the intra-cuff pressure can be considered.

In ventilation situations in which the ventilation pressure in the trachea (Ptrach) exceeds the intra-cuff pressure Pcuff, the respiratory pressure built up by the ventilator, for instance in pressure-supported ventilation or controlled modes of ventilation, can be oriented to the intra-cuff pressure of the cuff of a tracheal tube introduced into the trachea of the patient, which pressure is a controlling measured variable. By measuring the effective tracheobronchial airway pressure via the intra-cuff pressure, as shown by FIG. 1, the user gains a genuine parameter measured in the patient's lungs, and thus gains additional certainty and precision in ventilation with a ventilator, such as shown in FIG. 6.

If Ptrach is less than Pcuff, or if the cuff pressure can no longer reflect the course of the ventilation pressure, then the ventilator orients itself in the conventional way to the proximal airway pressure Pprox measured before the tube. In pressure-supported or pressure-controlled modes of ventilation, the entire course of the ventilation pressure can be oriented to the central course of the ventilation pressure.

With the pressure support by the ventilator, a tracheobronchial pressure is built up and controlled, and the desired pressure is maintained.

For optimizing the compensation for the flow-dependent resistance of the tracheal tube, the pressure difference between the tracheobronchial airway pressure at the tip of the tube (Ptrach) and the ventilation pressure (Pprox) measured at the proximal end of the tracheal tube is determined from one breathing stroke to another.

The conventional ventilation equipment option of so-called automatic tube compensation calculates a corresponding pressure difference to be imposed by the ventilator. The pressure difference is equivalent to the pressure required to overcome the flow-dependent flow resistance of the tube. It is oriented to a corrective constant that uses the inside diameter of the tracheal tube as a basis for calculation. The inside diameter of the tube is input manually at the onset of ventilation and is thus fixed over the further course of ventilation.

The automatic tube compensation is done by conventional technology in accordance with the following algorithm, for example, $\Delta P = \text{const} \times \text{flow}^2$, in which $\Delta P$ represents the compensatory pressure to be calculated.

Changes in the inside diameter of the tracheal tube, for example from partial kinking, or shifting/stopping up of the tracheal tube with secretion which creates resistance during ventilation, are not recognized by the compensatory algorithm in conventional ventilators and can be recognized by the user only in the form of an increase in the proximal ventilation pressure Pprox measured before the tube. The compensatory algorithm cannot, however, follow transitory changes in the inside diameter of the tube and thus in the flow resistance, and the result is compensation that is largely inappropriate to the actual situation.

According to this invention, $\Delta P$ to compensate for the flow-dependent tube resistance can be ascertained by measuring the airway pressure in the trachea (Ptrach) via the intra-cuff pressure, in those regions of the ventilation pressure curve where Ptrach exceeds the fill pressure of the cuff, Pcuff, or in other words in the range tx.

In this pressure range, $\Delta P$ can therefore be measured directly and without any relative chronological latency, using the equation $\Delta P = \text{Pprox} - \text{Pcuff}$, and is therefore superior to the above-described compensatory approximation based on a rigid, nondynamic constant.

In the ventilation pressure range above the cuff fill pressure, for example of 15 mbar at the cuff, the corrective constant const can be calculated continuously from the measured pressure difference $\Delta P$, by solving the equation for the constant const $(\text{const} = \text{flow}^2 : \Delta P)$.

The corrective constant thus ascertained can then be used for currently adapted compensation of the complete next breathing stroke (using the equation $\Delta P = \text{const} \times \text{flow}^2$).

Tracheal tubes and tracheostomy cannulas that have microthin-walled cuffs furthermore, in a patient who is spontaneously breathing, also make it possible to detect fluctuations in the intrathoracic pressure caused by the mechanics of breathing. The effect is especially pronounced whenever the cuff is placed in the thoracic segment of the trachea, as is almost always the case in patients with tracheostomies.

Particularly in small children and the newborn, intrathoracic pressure changes are transmitted virtually simultaneously and with relatively great amplitude via the tracheal wall (transmurally) to the cuff and thus affect its fill pressure.

The special sensing qualities of microthin balloon membranes for embodying the cuff of tracheal tubes and tracheostomy cannulas (or the balloons of gastric probes) make extremely sensitive, latency-free detection of such fluctuations in the intrathoracic pressure possible and open up additional options for controlling a ventilator.

Optimizing the synchronization of the ventilator and the patient can be considered.

To trip a supported machine breathing stroke, the patient, by breathing, must generate or trigger a predetermined inspiratory minimum flow, or minimum pressure drop in the tubing of the ventilator. In order to generate such a trigger signal, however, the patient must overcome not only the resistances of the thorax and the lungs and as an end-expiratory pressure (intrinsic PEEP) that can burden the already diseased lungs, but also the resistances of the ventilator tube and the delivery tubing.

Figure 2:
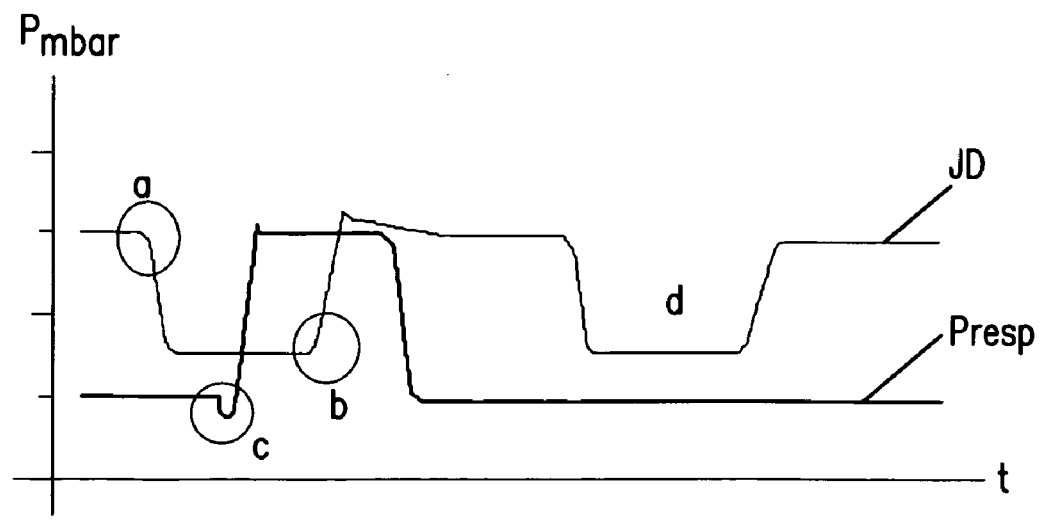
FIG. 2 is a graphical representation showing typical ventilation situations in conventional pressure-triggered and pressure-assisted ventilation.

In FIG. 2, a typical ventilation situation in conventional pressure-triggered, pressure-assisted ventilation is shown. The course over time is plotted on the horizontal axis T, and the pressure P is plotted in millibars on the vertical axis.

The upper curve ID shows the intra-esophageal (intrathoracic) pressure course.

The lower curve shows the airway pressure Presp.

The time a represents the onset of thoracic inspirational motion, the onset of inhalation.

The instant b marks the end of the thoracic inspirational motion, the onset of exhalation.

At c, a discrete attempt at inspiration by the patient causes a slight drop in the ventilation pressure in the tubing that supplies the patient. If this pressure drop exceeds a certain value (trigger threshold), the supporting breathing stroke is tripped. This is time-offset from the actual onset a of inspiration. The respiratory work performed by the patient in the interval between a and c can in many cases lead to respiratory fatigue of the patient. Frustrating attempts by the patient to breathe, during which because of the inadequate trigger sensitivity of conventional ventilators no supporting stroke can be tripped, only hasten respiratory fatigue.

Particularly in patients with existing pulmonary disease, such as obstructive pulmonary disease, the respiratory work that has to be done to trigger the ventilator can be considerable and can lead to physical respiratory fatigue in the patient. The assisted ventilation has therefore until now, in many cases, had to be repeatedly disrupted and then continued with intermittent alternation with a controlled, completely machine-specified mode of ventilation.

Moreover, particularly in patients with existing pulmonary disease, a large proportion of the respiratory efforts fail to be detected by the ventilator, even if the trigger thresholds are set quite sensitively, see FIG. 2. The thoracic breathing work is considerable but does not suffice to generate an equipment-triggering pulse (minimum gas flow/minimum pressure drop). The respiratory effort by the patient is therefore not supported by the ventilator.

According to this invention, it is possible to design the ventilation such that the interaction between the patient and the ventilator is optimized, and respiratory fatigue in assisted modes of ventilation is avoided, absolutely to the greatest extent possible.

If at the onset of inspiration the thoracic volume is increased (raising of the chest, lowering of the diaphragm), if a proportional drop in the intrathoracic pressure occurs, if the cuff of the tracheal tube or tracheostomy cannula is placed in the thoracic portion of the trachea, then the intrathoracic pressure is also transmitted through the tracheal wall to the cuff pressure.

If the pressure at the onset of inspiration drops by a predetermined, freely selectable value (trigger threshold), then the machine-supported breathing stroke is tripped. This shortens the length of time between a and c in FIG. 2. Because there is only a slight delay between the onset of the thoracic breathing effort and the onset of machine support, the triggering work to be performed in order to trip the supporting strokes can be reduced to a minimum. Trigger-dictated respiratory fatigue in the patient, as is observed above all in the phase of respiratory insufficiency at the instant of transition from long-term controlled ventilation to assisted ventilation, can thus be avoided.

The instant of triggering, ascertained both in the cuff and in the tubing of the ventilator, can be compared in the ventilator, or its control device, and if a no longer plausible difference, such as the trigger time cuff pressure, is exceeded, for instance if the triggering instance cuff pressure occurs later than the triggering instant in the tubing, or in the event of complete asynchronism, this leads to an alarm or a discontinuance of the cuff-triggered ventilation, and a switchover to a conventional trigger mode.

To further shorten the chronological latency between the onset of thoracic respiratory effort and the onset of machine support, this invention proposes the alternative triggering on the basis of an autocorrelative recognition of a curve segment typical for the onset of inspiration (the initial drop in the intra-cuff pressure curve at the onset of thoracic breathing). This pattern curve segment is compared with the ongoing intra-cuff pressure signal by an autocorrelation algorithm.

The correlation coefficients (from 0 to +1) ascertained serve as a trigger criterion. The user specifies a minimum correlation to be attained as the trigger threshold (for instance, +0.88). If this value is reached, the supporting machine stroke begins. The pattern curve segment to be correlated can be averaged at regular intervals (arithmetic averaging) or on a continuous sliding basis (for instance, a running average) from a selectable number of previous inspiratory curve segments.

This invention combines triggering on the basis of thoracic pressure fluctuations (via the cuff of the tracheal tube or tracheostomy cannula, or via the esophageal balloon of a suitably equipped gastric probe) with an intermittent mandatory pressure-supported ventilation.

In the ventilation mode of this invention, the number of machine-assisted breathing strokes per minute is specified by the user (mandatory ventilation). Based on the number of mandatory ventilation strokes, the minute is divided into intervals of equal duration (time slots). Within these time slots, only a single machine-assisted breathing stroke at a time can be tripped by the patient. All the other respiratory efforts or respiratory excursions of the patient within this time slot are unsupported by the ventilator. The respiratory work is then predominantly done by the patient within the context of these breaths that are not machine-supported.

Triggering the ventilator on the basis of intrathoracic pressure fluctuations caused by respiratory mechanics can also be done using a gastric probe with an esophageal balloon, as described in German Patent Reference DE 197 24 096 A, which is used for long-term, functionally organically tolerated balloon secretion sealing (no transporting of the balloon toward the stomach, no relevant pressure maximums inside the balloon during peristaltic contractions).

With such a balloon placed esophageally, changes in the intrathoracic pressure course can also be monitored, and the measured esophageal balloon pressure can be made useful, in the same way as the intra-cuff pressure, for controlling the assisted ventilation.

Machine compensation for respiratory efforts that are not, or are only slightly, flow-effective or volumetrically effective, are discussed below.

To enable the early transition to an assisted ventilation pattern upon even the least independent breathing by the patient, a ventilator should have the option of maximally relieving the respiratory mechanics of the patient as needed.

This invention thus proposes compensating for spontaneous, nonsupported respiratory efforts with insufficient or low volumetric performance (insufficient tidal volume without affecting gas exchange) by an adapted machine ventilation stroke, in such a way that in conjunction with the pressure measurement values obtained from the esophageal balloon of the gastric probe, the esophageal balloon pressure curve in the course of the thoracic inspiratory motion is returned to the range of the basal, neutral balloon fill pressure of the gastric probe. The respiratory work done in the context of nonsupported respiratory efforts can thus be largely neutralized by machine compensation, referring to FIG. 3.

Figure 3:
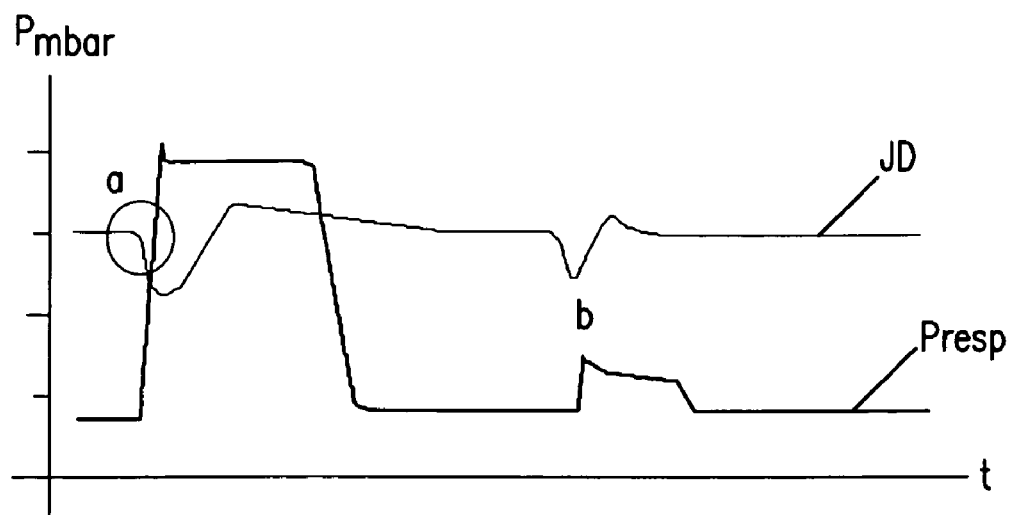
FIG. 3 is a graphical representation showing the ventilation situation in esophageally triggered and pressure-assisted ventilation.
Figure 4:
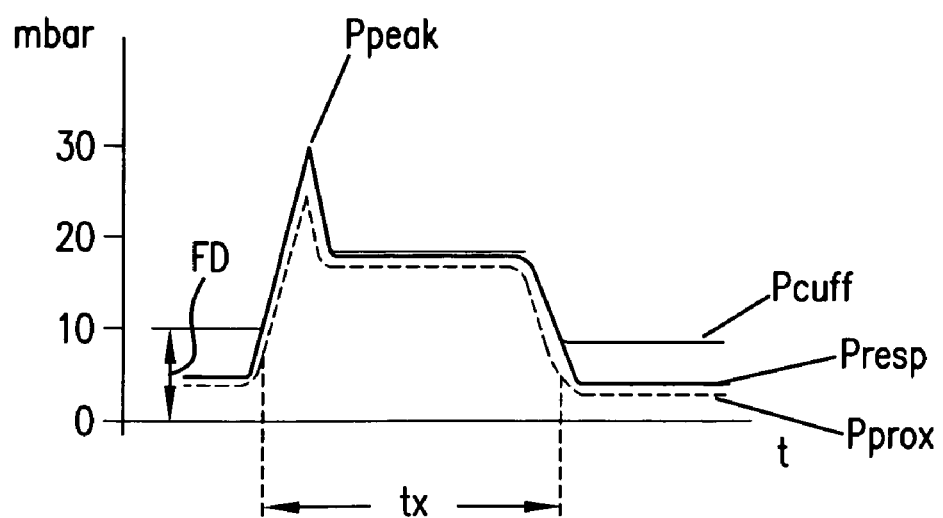
FIG. 4 is a graphical representation showing the various pressure courses of a breathing stroke for the sake of direct measurement of ΔP (pressure drop along the tube from flow-dependent flow resistance in the tube lumen)

In FIG. 3, the minimized triggering work in esophageally triggered pressure-assisted ventilation is shown. Here the respiratory neutralization of unproductive, unsupported inspiratory efforts is shown. The upper course represents the intra-esophageal (intrathoracic) pressure course ID.

The lower curve shows the airway pressure Presp attained by the assisted ventilation.

In the range a, the triggering ensues as a result of a drop in esophageal pressure upon the onset of thoracic inspiratory motion; the chronological latency until the onset of machine ventilation is therefore minimally small (minimal triggering work by the patient).

At b, a breathing stroke that neutralizes the patient's breathing mechanism is shown, which after esophageal triggering, by suitably adapted course of ventilation pressure, returns the esophageal pressure curve to the baseline (position of repose). The thoracic breathing work performed by the patient during an inspiratory effort is thus reduced to the greatest possible minimum, and the tidal volume also is in the range of idle volume ventilation; no gas exchange, or no relevant gas exchange, takes place. The intrathoracic pressure course ID is ascertained by measuring the esophageal balloon pressure of the gastric probe inserted into the esophagus. The compensatory success of a ventilation stroke adapted in this way is oriented and fed back to the intra-esophageal pressure course.

The compensation could, for instance if combined with intermittent mandatory pressure-supported ventilation, be designed so that it becomes active after the conclusion of a mandatory stroke and remains active until the end of a given time slot.

With synchronized intermittent mandatory pressure-assisted ventilation and compensation or neutralization activated in this way, the patient's respiratory work then occurs solely in the context of the machine pressure-supported mandatory strokes. By adapting the machine support (for instance varying the initial inspiratory flow and/or the inspiratory ventilation pressure) in a way oriented to the patient's respiratory work graph (tidal volume over esophageal balloon pressure), the proportion of independent respiratory work to these mandatory strokes can likewise be reduced to a minimum.

Thus the training of the patient's respiratory work can be adapted, based on a state of maximum possible respiratory relief, incrementally to the gradually increasing respiratory performance of the patient.

For example, such ventilation planning could begin with an intermittent reduction in the support by the mandatory strokes (reduction in the initial flow and/or inspiratory pressure). If sufficient breathing by the patient persists (which can be detected from the increased thoracic deflection in the work graph and from the virtually constant tidal volume), the machine support in the form of the mandatory strokes can be increasingly restricted. In addition, the machine compensation for (neutralization of) spontaneous nonsupported breathing strokes can be reduced incrementally or terminated. In a final phase, by reducing the number of supported mandatory breathing strokes, the training performance of the patient can then be increased by the correspondingly increased number of unsupported breathing strokes, until finally the mandatory strokes can be dispensed with entirely.

Monitoring the patient's respiratory work is discussed below.

Respirators and ventilators of conventional design are not equipped to monitor the patient's respiratory work on the basis of genuine respiratory function parameters measured in the patient. Although the respirator does ascertain such variables as tidal volume, ventilation pressure and the breathing flow, a characterization to be achieved intuitively by the user of the current or medium-term and long-term effect of a selected ventilation regime on the respirator efficiency of the patient, however, has until now been unavailable.

In conventional monitoring, the respiratory fatigue of the patient cannot be prevented in advance by correcting the machine ventilation parameters, as a rule. The success or failure of a ventilation regime has thus until now been predominantly interpreted from the clinical aspect (onset of respiratory fatigue with tachypnea) or changes in the blood gases (respiratory acidosis).

As an essential component of this invention, a continuous characterization of respiratory work curves (esophageally via the tidal volume) in a special form is proposed, as a quasi-optimized interface with the user, and these curves can then be shown for instance on a monitor M in a ventilator as shown in FIG. 6.

One goal of the respiratory monitoring according to this invention is the earliest possible transition from a controlled to an assisted form of ventilation, or faster weaning from the respirator in a way oriented strictly to the mechanical respiratory performance of the patient.

It is preferable according to this invention for spontaneously machine-supported and unsupported breathing strokes to be plotted on the same coordinate system as the work graph.

The work graphs of individual pressure-supported breathing strokes show whether the current choice of parameters (initial inspiratory volumetric flow, inspiratory pressure to be attained, PEEP) lead to the desired scope of respiratory relief of the breathing strokes of the patient.

The respiratory work graphs of non-machine-supported breathing strokes, conversely, make an approximate assessment of the successive respiratory training possible (decreasing respiratory work (respiratory fatigue), stagnant or increased respiratory work (further reduction in machine support)).

To integrate the course over time (trend) in the respiratory work with the monitor unit (cyclical respiratory work graphs) for the sake of ventilation planning, this invention proposes the following modes of characterization.

The applicable current respiratory work cycles are shown in the form of an uncorrected original signal, for instance in the color red. In order to characterize the effective training for the particular equipment setting in an easily interpreted way via a medium-term to long-term period on the monitor, the respiratory cycles (loops) are statistically averaged every 5 minutes, for instance, and the resultant loop is then shown on the monitor in the form of a representative respiratory work curve for the applicable period of time. The loop is assigned a particular color value, such as light blue.

The procedure is then continued in the same way with the respiratory cycles in ensuing time intervals. The loop then calculated is assigned the same color value as the preceding curve (light blue). The color value of the preceding loop, conversely, then shifts successively to a darker blue value. The respiratory history of the patient can thus be integrated into the monitor unit in a way that is easy for the user to interpret, from the shift in the color values, for instance from light blue to dark blue.

The ventilation parameters used during a time segment can be made visible, for instance by activating the appropriate loop in a window on the screen.

Optionally, the color change from light to dark, in the cycles averaged every 5 minutes, for instance, can be done exclusively in the event of changes in the ventilation parameters.

To display and check the synchronization of the patient and the respirator, it is optionally possible to incorporate the ventilation pressure and/or ventilation flow (measured in the machine system) and the intrathoracic pressure (measured in the esophageal balloon) into the display, in the form of a curve over time.

It is also conceivable for the absolute value of the respiratory work performed in supported and unsupported strokes to be displayed (in each case as a separate curve) in joules over time.

Spontaneous stationary, non-peristaltic, so-called secondary contractions of the esophagus are expressed, in the intrathoracic pressure curve, by brief, steeply rising pressure increases.

Such curve courses can be detected as such from predetermined autocorrelation patterns and recorded in terms of their frequency. They do not enter into the statistical averaging of the loops and are either not shown, or shown only optionally, in the display on the monitor.

In a corresponding way, peristaltic or so-called primary contractions of the esophagus are detected and handled as gradually rising and falling intra-esophageal pressure increases that last several seconds.

The monitoring according to this invention can also be used, in conventionally triggered, pressure-supported modes of ventilation, in so-called BIPAP ventilation, or in proportionally assisted ventilation (PPSV), for a choice of ventilation parameters that is oriented closely to the current respiratory capacity of the patient.

In conventional assisted ventilation patterns, it is known that the patient inhalation is in many cases not yet concluded while the respirator is already in the exhalation mode. The converse case of machine-assisted ventilation beyond the end of the inhalation efforts by the patient is also often observed. The autocorrelative signal analysis of the intra-esophageal pressure curve for instance also makes it possible to terminate the assisted ventilation stroke synchronously with the conclusion of the thoracic inspiratory motion on the part of the patient.

Analogously to the onset of ventilation, the duration of the assisted stroke can be adapted to the patient's breathing (correlation of the continuous intra-esophageal pressure signal with a pattern signal that is morphologically typical for the end of inspiration).

Two work graphs according to this invention, schematically shown in FIGS. 7 and 8, and possible ventilation situations are described as examples. In FIG. 7, a spontaneous, intermittent mandatory pressure-supported ventilation is shown which is typically called pressure support ventilation, or PSV.

In the work graph of FIG. 7, the tidal volume is plotted in ML on the vertical coordinate, over the esophageal balloon pressure Pesoph in mmHg, plotted horizontally, is plotted as a work graph for the respiratory work of the patient. The respiratory cycles are shown as a loop, specifically by statistical averaging over 5 minutes. The current loop in each case is shown unaveraged and in red as an original signal over a respiratory window (60 sec./number of mandatory strokes).

The averaged loops, each representing an interval of a specified number of minutes, such as 5 minutes, are designated by a through d and pertain in FIG. 7 to unassisted spontaneous breathing.

The loops marked A through D in FIG. 7 relate to mandatory machine pressure-supported spontaneous breaths. Individually, the loops are as follows:

(a) pronounced thoracic respiratory excursions with low tidal volume (idle volume breathing) corresponding to dark blue;

(A) high inspiratory pressure with resultant high tidal volume, extensive respiratory relief of the patient's respiratory musculature reduction in the assisted component (pressure support);

(b) compensation for the low respiratory minute volume by supported respiratory work in the unassisted spontaneous breaths (increased tidal volume);

(B) tidal volume drops; partial compensation for the supported component by forced respiratory work by the patient (increased thoracic respiratory work) positive training effect at constant machine parameters;

(c) increase in the non-supported respiratory work by the patient with increasing tidal volume;

(C) increasing contribution by the patient to the breathing stroke with an increase in the tidal volume further reduction in the pressure support;

(d) progressive success in training, increasing tidal volume with constant thoracic respiratory work corresponding to light blue; and (D) the reduction in the pressure support is compensated for while the tidal volume stays constant.

One goal is gradual approximation of the unsupported and the supported respiratory work curves.

In FIG. 8, the work graph is shown for a flow-compensated and volume-compensated patient ventilation in the proportional pressure support or PPS mode. Once again, the tidal volume here is plotted over the esophageal balloon pressure. The loops a through e shown are each representative of an interval of predetermined minutes, such as 5 minutes, and relate to proportional flow-compensated and volume-compensated assisted ventilation. Individually, the loops show the following:

(a) The patient is too weak to generate a volumetric flow which means that for such patients, PPS is unsuitable. A change to an esophageally triggered pressure-supported ventilation, such as the PSV mode, is necessary; and (b) The loops b through e show that the patient does generate an adequate volumetric flow; continuous increase in the respiratory work is brought about by incremental empirical adaptation of the options of flow-compensation and volumetric-compensation of the PPS mode to the pulmonary elasticity and resistance.

A monitor M, which shows the work graphs of FIGS. 7 and 8, can for example, be assigned to the control device of the ventilator of FIG. 6. Accordingly, the requisite patient parameters should then be measured and supplied to the control device.

The invention claimed is:

1. In a method for controlling a flow of breathing gas in a ventilator for assisted or controlled ventilation of a patient as a function of a tracheobronchial airway pressure of the patient, having one of a ventilator tube, a tracheal tube and a tracheostomy tube, which can be introduced into a trachea of the patient and can be subjected to the breathing gas and which has an inflatable cuff and at least one lumen that is continuous from a distal end of the ventilator tube to a proximal end of the ventilator tube, and wherein an airway pressure is detected, the improvement comprising: determining the tracheobronchial airway pressure by one of continuous and intermittent detection and evaluation of an intra-cuff pressure prevailing in the cuff of the tube inserted into the trachea, and controlling the flow of the breathing gas in the ventilator as a function of a detected intra-cuff pressure, determining a pressure difference ($\Delta P$) generated by the ventilator to overcome a flow resistance of the tube as a function of the pressure difference between the pressure at the proximal end of the tube and the tracheobronchial airway pressure at the distal end of the tube by measurement of the pressure at the proximal end of the tube and the intra-cuff pressure, and using a $\Delta P$ to calculate a compensatory constant, and adapting dynamically the compensatory constant from one breathing stroke to another breathing stroke during respiration by the ventilator, to a respective current flow resistance of the tube.

2. In the method of claim 1 wherein the cuff is subjected to a fill pressure $\leqq 25$ mbar.

3. In the method of claim 2, wherein the cuff is subjected to a fill pressure $\leqq 15$ mbar.

4. In the method of claim 3, wherein the tube with the cuff of a stretchable thin plastic film with a wall thickness of less than 0.02 mm is used.

5. In the method of claim 4, wherein the cuff is made from a film of thermoplastic polyurethane elastomer with a modulus of tension of at least 10 MPa at 300% expansion in accordance with ASTM D 412, and is used for the tube.

6. In the method of claim 5, wherein a differential value that trips a breathing stroke of the ventilator is specified in a cuff fill pressure as a trigger threshold for the ventilator, and if an intra-cuff pressure drops during an onset of thoracic inspiration by the patient to below the trigger threshold the ventilator is activated and trips a machine-supported breathing stroke.

7. In the method of claim 6, wherein during controlled respiration, values obtained by measuring the intra-cuff pressure are used to control an upper pressure function of the upper pressure limit (Pmax) of the ventilator so that the ventilator on attaining a predetermined upper pressure one of switches off a delivery of the breathing gas and switches over to exhalation.

8. In the method of claim 7, wherein for optimizing control of the ventilator, a gastric probe having an inflatable balloon that can be subjected to a fill pressure of $\leqq 25$ mbar is introduced into an esophagus of the patient, and an esophageal balloon pressure prevailing in the balloon of the gastric probe is detected one of continuously and intermittently, and pressure fluctuations in an intrathoracic pressure transmitted to the gastric probe balloon are detected and evaluated and supplied to the ventilator for controlling the flow of breathing gas.

9. In the method of claim 8, wherein the intra-cuff pressure of the tube is measured by a measuring instrument, and measured values are transmitted by a measuring line that extends from the cuff of the tube to one of the ventilator and a control device for the ventilator.

10. In the method of claim 9, wherein the esophageal balloon pressure in the balloon of the gastric probe introduced into the esophagus is measured and second measured values are transmitted from the balloon to one of the ventilator and a control device for the ventilator.

11. In the method of claim 10, wherein values obtained by measuring the esophageal balloon pressure are used to ascertain a respiratory work done by the patient, and from breathing strokes pressure-supported by the ventilator of respiratory cycles of fixed duration cyclical breathing work diagrams are determined and displayed on a monitor as one of loops and areas.

12. In the method of claim 1, wherein the cuff is subjected to a fill pressure $\leqq 15$ mbar.

13. In the method of claim 1, wherein the tube with the cuff of a stretchable thin plastic film with a wall thickness of less than 0.02 mm is used.

14. In the method of claim 1, wherein the cuff is made from a film of thermoplastic polyurethane elastomer with a modulus of tension of at least 10 MPa at 300% expansion in accordance with ASTM D 412, and is used for the tube.

15. In the method of claim 1, wherein a differential value that trips a breathing stroke of the ventilator is specified in a cuff fill pressure as a trigger threshold for the ventilator, and if an intra-cuff pressure drops during an onset of thoracic inspiration by the patient to below the trigger threshold the ventilator is activated and trips a machine-supported breathing stroke.

16. In the method of claim 1, wherein for optimizing control of the ventilator, a gastric probe having an inflatable balloon that can be subjected to a fill pressure of $\leqq 25$ mbar is introduced into an esophagus of the patient, and an esophageal balloon pressure prevailing in the balloon of the gastric probe is detected one of continuously and intermittently, and pressure fluctuations in an intrathoracic pressure transmitted to the gastric probe balloon are detected and evaluated and supplied to the ventilator for controlling the flow of breathing gas.

17. In the method of claim 1, wherein the intra-cuff pressure of the tube is measured by a measuring instrument, and measured values are transmitted by a measuring line that extends from the cuff of the tube to one of the ventilator and a control device for the ventilator.

18. In a method for controlling a flow of breathing gas in a ventilator for assisted or controlled ventilation of a patient as a function of a tracheobronchial airway pressure of the patient, having one of a ventilator tube, a tracheal tube and a tracheostomy tube, which can be introduced into a trachea of the patient and can be subjected to the breathing gas and which has an inflatable cuff and at least one lumen that is continuous from a distal end of the ventilator tube to a proximal end of the ventilator tube, and wherein an airway pressure is detected, the improvement comprising: determining the tracheobronchial airway pressure by one of continuous and intermittent detection and evaluation of an intra-cuff pressure prevailing in the cuff of the tube inserted into the trachea, and controlling the flow of the breathing gas in the ventilator as a function of a detected intra-cuff pressure, and during controlled respiration, using values obtained by measuring the intra-cuff pressure to control an upper pressure function of the upper pressure limit (Pmax) of the ventilator so that the ventilator on attaining a predetermined upper pressure one of switches off a delivery of the breathing gas and switches over to exhalation.

19. In the method of claim 18, wherein a pressure difference ($\Delta P$) generated by the ventilator to overcome a flow resistance of the tube is determined as a function of the pressure difference between the pressure at the proximal end of the tube and the tracheobronchial airway pressure at the distal end of the tube by measurement of the pressure at the proximal end of the tube and the intra-cuff pressure, and a ΔP is used to calculate a compensatory constant, and the compensatory constant is adapted dynamically from one breathing stroke to another breathing stroke during respiration by the ventilator, to a respective current flow resistance of the tube.

20. In a method for controlling a flow of breathing gas in a ventilator for assisted or controlled ventilation of a patient as a function of a tracheobronchial airway pressure of the patient, having one of a ventilator tube, a tracheal tube and a tracheostomy tube, which can be introduced into a trachea of the patient and can be subjected to the breathing gas and which has an inflatable cuff and at least one lumen that is continuous from a distal end of the ventilator tube to a proximal end of the ventilator tube, and wherein an airway pressure is detected, the improvement comprising: determining the tracheobronchial airway pressure by one of continuous and intermittent detection and evaluation of an intra-cuff pressure prevailing in the cuff of the tube inserted into the trachea, and controlling the flow of the breathing gas in the ventilator as a function of a detected intra-cuff pressure, measuring an esophageal balloon pressure in the balloon of the gastric probe introduced into the esophagus and transmitting second measured values from the balloon to one of the ventilator and a control device for the ventilator, and measuring values obtained by the esophageal balloon pressure and using the values to ascertain a respiratory work done by the patient, and from breathing strokes pressure-supported by the ventilator of respiratory cycles of fixed duration determining cyclical breathing work diagrams and displaying them on a monitor as one of loops and areas.

* * * * *